US006997578B2

(12) United States Patent  (10) Patent No.: US 6,997,578 B2
Culbert et al.  (45) Date of Patent: Feb. 14, 2006

(54) ENVIRONMENTALLY RESISTANT GERMICIDAL SYSTEM

(75) Inventors: Robert Culbert, Manhattan Beach, CA (US); William Ryczek, Glendora, CA (US)

(73) Assignee: Steril-Aire, Inc., Burbank, CA (US)

( * ) Notice: Subject to any disclaimer, the term of this patent is extended or adjusted under 35 U.S.C. 154(b) by 160 days.

(21) Appl. No.: 10/751,090

(22) Filed: Jan. 2, 2004

(65) Prior Publication Data

US 2004/0223329 A1   Nov. 11, 2004

Related U.S. Application Data

(60) Provisional application No. 60/469,165, filed on May 9, 2003.

(51) Int. Cl.
 *F21S 8/00* (2006.01)
(52) U.S. Cl. .................. 362/263; 362/267; 362/362; 362/416
(58) Field of Classification Search ............. 362/263, 362/261, 267, 362, 416; 313/578, 567, 569, 313/613
 See application file for complete search history.

(56) References Cited

U.S. PATENT DOCUMENTS

| | | | |
|---|---|---|---|
| 2,922,137 A | 1/1960 | Krupp | |
| 3,926,556 A | 12/1975 | Boucher | |
| 4,384,236 A | 5/1983 | Hellwig | |
| 4,396,860 A | 8/1983 | Hellwig | |
| 4,667,276 A | 5/1987 | Cheng | |
| 4,762,613 A * | 8/1988 | Snowball | 210/192 |
| 4,878,854 A | 11/1989 | Cannon | |
| 4,953,066 A | 8/1990 | Schiffer | |
| 4,971,687 A | 11/1990 | Anderson | |
| 4,982,313 A | 1/1991 | Lupien | |
| 4,990,313 A | 2/1991 | Pacosz | |
| 5,151,174 A | 9/1992 | Weismann | |
| 5,334,905 A | 8/1994 | Ullrich | |
| 5,535,103 A | 7/1996 | Iiyama | |
| 5,550,718 A | 8/1996 | Shy | |
| 5,607,218 A | 3/1997 | Choji | |
| 5,660,719 A | 8/1997 | Kurtz | |
| 5,688,138 A | 11/1997 | Chuang | |
| 5,701,050 A | 12/1997 | Wolf | |

(Continued)

OTHER PUBLICATIONS

Leviton, Industrial Watertight Wiring Devices.

(Continued)

*Primary Examiner*—Sandra O'Shea
*Assistant Examiner*—Mark Tsidulko
(74) *Attorney, Agent, or Firm*—SoCal IP Law Group LLP; Steven C. Sereboff; Joel G. Landau

(57) ABSTRACT

Apparatus and methods for an environmentally resistant germicidal lamp are disclosed. A cover may have a material resistant to at least one of dripping, light splashing, light spraying of liquid and condensation. The cover may have a first section having an opening for receiving a base of a lamp, and an inner surface for encompassing and being slightly larger than an outer cross section of the base when the first section receives the base. The cover may have a second section having an opening for receiving a socket of an electric discharge lamp fixture, and an inner surface for encompassing and being slightly larger than an outer cross section of the socket when the second section receives the socket. The cover may shield and partially enclose electrical contacts of either the base or the socket from at least one of dripping, light splashing, light spraying of liquid and condensation.

17 Claims, 14 Drawing Sheets

U.S. PATENT DOCUMENTS

| | | |
|---|---|---|
| 5,729,078 A | 3/1998 | Pragt |
| 5,853,299 A | 12/1998 | Wu |
| 5,866,076 A | 2/1999 | Fencl |
| 5,902,552 A | 5/1999 | Brickley |
| 6,059,437 A | 5/2000 | Shibuya |
| 6,152,574 A | 11/2000 | Lin |
| 6,193,894 B1 | 2/2001 | Hollander |
| 6,221,314 B1 | 4/2001 | Bigelow |
| 6,280,686 B1 | 8/2001 | Scheir |
| 6,367,949 B1 | 4/2002 | Pederson |
| 6,372,186 B1 | 4/2002 | Fencl |
| 6,454,426 B1 | 9/2002 | Altman |
| 6,520,790 B1 | 2/2003 | Okanoto |
| 6,580,228 B1 * | 6/2003 | Chen et al. ............. 315/185 R |
| 2004/0161371 A1 * | 8/2004 | Russell et al. ............. 422/121 |

OTHER PUBLICATIONS

Leviton, Wetguard.

Leviton, Pin & Sleeve Device Features.

Leviton, Pin & Sleeve Devices Product Line Bulletin.

Home Depot, PVC Elbow.

Ahsupply.com, 36 or 55 watt Bright Kit.

* cited by examiner

ENVIRONMENTALLY RESISTANT GERMICIDAL SYSTEM

RELATED APPLICATION INFORMATION

This application claims priority from Provisional Application No. 60/469,165, filed May 9, 2003, which is incorporated herein by reference.

NOTICE OF COPYRIGHTS AND TRADE DRESS

A portion of the disclosure of this patent document contains material which is subject to copyright protection. This patent document may show and/or describe matter which is or may become trade dress of the owner. The copyright and trade dress owner has no objection to the facsimile reproduction by any one of the patent disclosure as it appears in the Patent and Trademark Office patent files or records, but otherwise reserves all copyright and trade dress rights whatsoever.

BACKGROUND OF THE INVENTION

1. Field of the Invention

The present invention relates generally to environmentally resistant germicidal systems, and more particularly the invention relates to such devices used in air and surface sterilization.

2. Description of Related Art

One industry that is mature and economically sensitive to costs is the heating, ventilation and air conditioning (HVAC) industry. Because of the competitive nature of both the construction and HVAC industries, HVAC systems must be inexpensive to purchase and install. Of a more global interest though, is the cost to operate and maintain HVAC systems. Often, a building owner will replace an aging HVAC system as the reduction in operating and maintenance costs can offset the retrofit cost, sometimes in a matter of months.

Broad social and energy policies also favor efficient HVAC systems. In these days of electricity conservation and deregulation, it has become even more important to conserve energy consumption. Recently, entire electrical grids have shut down on very hot days in part because of the huge electrical demand from inefficient HVAC systems running at extreme capacity. Furthermore, energy conservation translates directly into improved environmental conditions and decreased reliance upon foreign petroleum.

HVAC systems are typically comprised of a cooling and heating section for, respectively, cooling and heating the air. An HVAC system will also include fans and ductwork for moving this conditioned air where it is needed. In most HVAC systems, air is drawn in, filtered, cooled and dehumidified or heated and humidified, and then delivered to a space. The greatest portion of this air is drawn from the space for recirculation through the HVAC system.

One factor impacting design and operation of HVAC systems is indoor air quality (IAQ). A major consideration in IAQ today is the amount of outdoor air introduced by an HVAC system into an otherwise sealed space. The HVAC industry and others have adopted standards for the introduction of outdoor air into spaces serviced by an otherwise closed HVAC system. These include offices, residential, commercial, industrial and institutional spaces, and modes of transportation such as cars, buses, planes and ships. In addition to controlling indoor air for occupant comfort, the goal of most HVAC systems is to provide air with reduced levels of particulate, gases and bioaerosols, be it for semiconductor, pharmaceutical or food processing facilities, hospitals, schools or offices and now the home.

Besides IAQ standards that include HVAC systems, there are numerous other standards that apply to HVAC systems, their design, construction and components. One set of standards that applies to HVAC (and other) electrical equipment has been promulgated by the National Electrical Manufacturers Association (NEMA). NEMA has published standards regarding enclosures for electrical equipment including HVAC equipment installed outdoors. A NEMA Type 4 enclosure is constructed for outdoor use and provides a degree of protection against rain, sleet, snow and the formation of ice. A NEMA Type 4 enclosure also provides a degree of protection against windblown dust, dirt, splashing water, hose-directed water and corrosion. A NEMA Type 4 enclosure should protect personnel against incidental contact with the enclosed equipment. Additional information is available from the NEMA Web site at www.nema.org.

One common use of germicidal lamps is in water treatment. The ultraviolet tubes are enclosed in a quartz sleeve. This is necessary because the water would otherwise draw heat away from the tube in the same manner as air or as in skin effect cooling.

Germicidal lamps for water treatment must have some amount of protection from the water itself. In particular, these lamps are sleeved and further isolated in some manner to be water tight against and compared to the water vessel in which the tube is installed. However, water application fixtures have not been considered or used in air treatment systems. Also, water application fixtures have not been produced for HVAC use or for air treatment use.

It is common for germicidal systems for air purification to be installed outdoors in the proximity with an HVAC systems ductwork, condenser or compressor. Outdoor installation may subject the electrical components of the germicidal system to environmental elements such as condensation, dripping water, splashing water, light spraying of cleansers, dripping oil, falling dirt, windblown dust, and windblown sand. An example of germicidal system designed to protect electrical components from harsh environmental elements is described in U.S. Pat. No. 6,372,186, Germicidal Lamp for Harsh Environments.

It is also common for germicidal systems for air purification to be installed indoors at hospitals, office buildings, food processing plants, and schools. Because such systems are not subject to harsh outdoor environments a NEMA 4×enclosure may be cost prohibitive to protect the electrical components.

DETAILED DESCRIPTION OF THE INVENTION

Throughout this description, the embodiments and examples shown should be considered as exemplars, rather than limitations on the apparatus and methods of the present invention.

Figure 1:
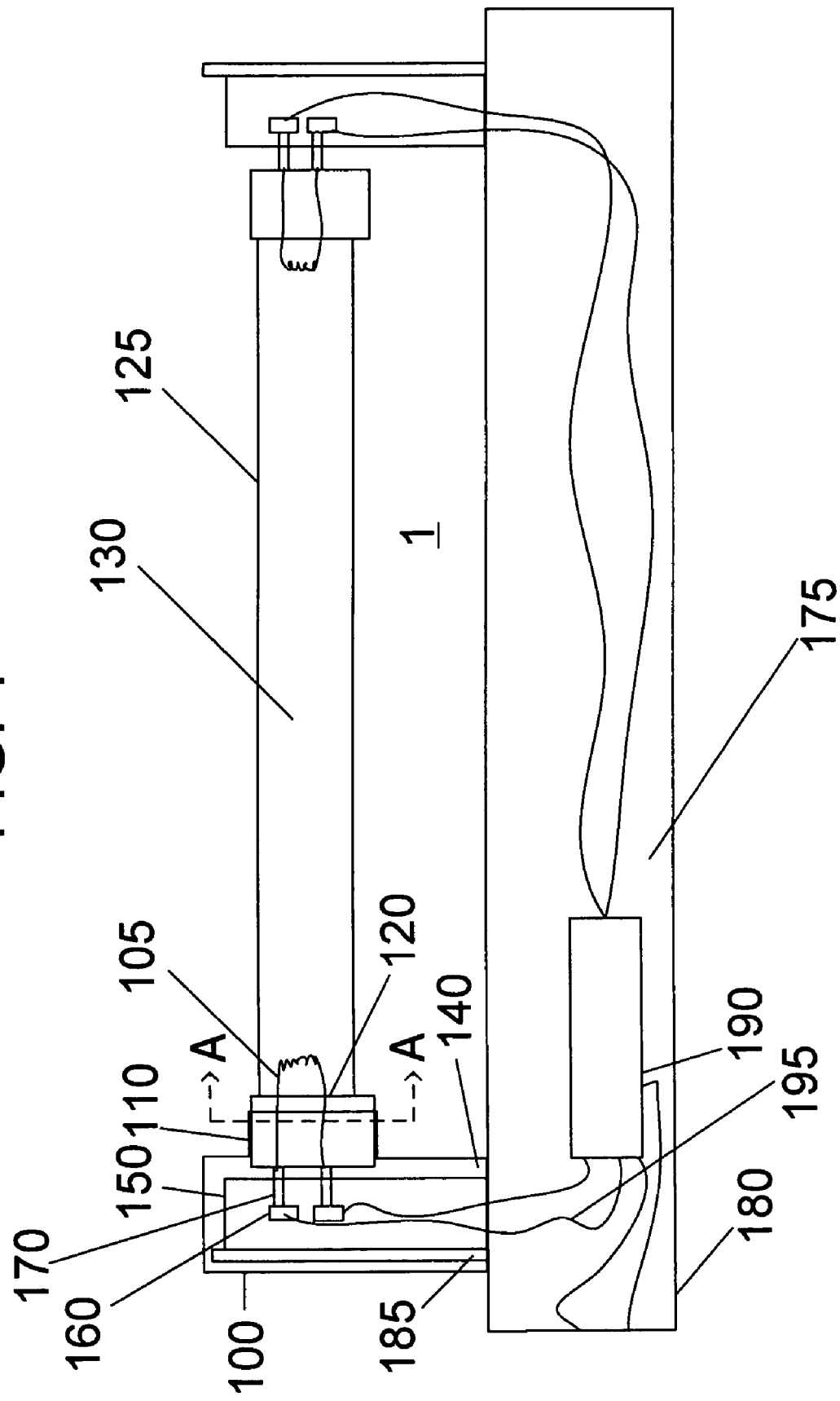
FIG. 1 is a perspective view of a first system in accordance with the invention.

Referring now to FIG. 1, there is shown an apparatus 1 including a cover 100, a lamp 130 and a fixture 175. The apparatus 1 may be for home use, industrial use, heating ventilation and air conditioning use, air purification use, surface treatment use, and food processing use. The apparatus 1 may be a germicidal lamp that kills viruses, bacteria, and molds. Alternatively, the apparatus 1 may kill other microbes that are airborne.

The lamp 130 may have a base 120 and a tube 125. The tube 125 construction may be a single walled envelope attached to the base 120. The tube 125 may enclose a vaporizable material such as mercury. The vaporizable material may emit ultraviolet light at a germicidal wavelength, for example 254 nm or 187 nm. The lamp 130 may be output biased for operation at low temperature. The tube 125 may emit at least one of visual light, infrared light, and ultraviolet light. The vaporizable material may be vaporized by an electrode 105 that is disposed within the lamp 130. The electrode 105 may be electrically connected to an electrical contact 170 of the base 120. The lamp 130 may operate where the vaporized material remains at a low or medium pressure.

The fixture 175 may have a housing 180, a socket 150, and a flange 185. The socket 150 may be attached to the housing 180. The socket 150 may be attached to the flange 185. The flange 185 may be attached to the housing 180. The flange 185 may be integral or fastened to the housing 180. The flange 185 may be welded to the housing 180.

The housing 180 provides mechanical support for the germicidal system. The housing 180 may be rigid. The housing 180 may be constructed of metal, plastic, ceramic, or glass. The housing 180 material may be a composite material. The choice of material should be made based on the environment that the housing 180 will be exposed to. The material of the housing 180 should be resistant to heat, light, and environmental elements such as dripping liquid, light splashing of liquid, light spraying of liquid and condensation. Examples of suitable materials may be stainless steel, aluminum, and PVC.

The flange 185 may be constructed of metal, plastic, ceramic, glass, or a composite material. The material of the flange 185 is not required to be the same material as the housing 180. The choice of material may be made based on the environment that the flange will be exposed to. The material of the socket 150 should be resistant to heat, light, and environmental elements such as dripping liquid, light splashing of liquid, light spraying of liquid and condensation. Examples of suitable materials may be aluminum, steel or PVC.

The socket 150 may be constructed of metal, plastic, ceramic, glass, or a composite material. The material of the socket 150 is not required to be the same material as the housing 180. The choice of material may be made based on the environment that the socket 150 will be exposed to. The material of the socket 150 should be resistant to heat, light, and environmental elements such as dripping liquid, light splashing of liquid, light spraying of liquid and condensation. Examples of suitable materials may be fiberglass, silica fiber, and ceramic. The socket 150 may have an electrical contact 160 that is electrically connected to a power supply 190.

The power supply 190 may be mounted inside the housing 180. Alternatively, the power supply 190 may be located remote to the housing 180. The power supply 190 is for providing AC power to the electrode 105 of the lamp 130. The electrical circuit may comprise the power supply 190, wiring 195, an electrical contact 160 of the socket 150, an electrical contact 170 of the base 120 and the electrode 105. The electrical connection between the power supply 190 and the electrical contact 160 of the socket 150 may be achieved via wiring 195, direct physical connection, or otherwise. The electrical contact 170 of the base 120 may be electrically connected with the electrical contact 160 of the socket. The electrode 105 may be electrically connected with an electric contact 170 of the base 120.

The socket 150, when engaged with the base 120, may provide mechanical support to the base 120. The socket 150 may provide mechanical support directly to an electrical contact 170 of the base 120 or the base 120 itself. Alternatively, a lamp holder that is attached to the flange 185 may provide mechanical support to the base 120. A lamp holder may be made of a wire band that mechanically engages the base 120. The lamp holder may be a plastic member that frictionally engages the base 120. The lamp holder may be a magnet that retains the base 120 in the assembly.

The electrical contact 160 of the socket 150 and an electrical contact 170 of the base 120 may take an industry standard form which may be a bi-pin, a single pin, a R17d, a medium bi-pin, a four pin, a 2Gx13, a recessed double contact, a G-23, or a 2G-11.

The cover 100 may be manufactured from a material that is resistant to at least one of dripping liquid, light splashing of liquid, light spraying of liquid and condensation. The liquid may be water. Alternatively it may be a mixture of water and oil. Moreover, the liquid may be a solution of water and a solute. The solute may be a salt. The liquid may be a household cleaner or an industrial degreaser. The material may be glass, plastic, polymer, rubber, ceramic, metal or other material. The material may be elastic or rigid. Based on the use of the cover 100, the material selected may be suitable for exposure to temperature and or light. For example, the light may be infrared, visual light or ultraviolet light. The temperature may be very cold, such as −40 degrees Celsius. The temperature may be very hot, such as 150 degrees Celsius.

The cover 100 may have a first section 110 that at least partially surrounds the base 120 of the lamp 130. The cover 100 may have a second section 140 that at least partially surrounds the socket 150 of the fixture 175.

The cover 100 may include a first flange or skirt (not shown) at its point of interface with the housing 180. The first flange or skirt may flare out approximately $\frac{1}{8}^{th}$ of an inch from the main body of the cover 100 and be approximately $1/16^{th}$ of an inch thick. The dimensions of the first flange or skirt may vary depending on the amount of surface area contact desired between the cover 100 and the housing 180. Alternatively, the cover 100 may have a first flange or skirt (not shown) at its point of interface with the socket 150 of the fixture 175.

The cover 100 may include a second flange or skirt (not shown) at its point of interface with the base 120 of the lamp 130. The second flange or skirt may flare out $1/8^{th}$ of an inch from the main body of the cover 100 and be $1/16^{th}$ of an inch thick. The dimensions of the second flange or skirt may vary depending on the amount of surface area contact desired between the cover 100 and the base 120.

The cover 100 may include an alignment mark (not shown), which may ease installation of the cover 100 onto the socket 150 or onto the flange 185. Alternatively, the cover 100 may include a ridge along an inner surface of the cover. The ridge may function as a key and may ease installation of the cover 100 onto the socket 150 or onto the flange 185.

The cover 100 may also include an alignment mark (not shown), which may ease installation of the cover 100 onto the base 120. Alternatively, the cover 100 may include a ridge along an inner surface of the cover. The ridge may function as a key and may ease installation of the cover 100 onto the base 120.

The cover 100 shields the electrical contact 160 of the socket 150 and the electrical contact 170 of the base 120 from at least one of dripping liquid, light splashing of liquid, light spraying liquid, and condensation. The cover 100 may be installed on existing germicidal systems that may degrade or fail due to dripping liquid, light splashing of liquid, light spraying liquid, and condensation.

As shown in FIG. 1, the cover 100 is disposed on the left hand side of the environmentally resistant germicidal system. A cover may be provided on the right hand side of the system as well. Alternatively, a cover may be provided on both the left and right sides of the system. The choice of whether to provide a cover on the left side, right side, or both sides of the apparatus 1 may depend upon the environmental elements that the apparatus 1 is or might be exposed to and where on the apparatus 1 the exposure is or might occur.

As the cover 100 shields liquids from coming in contact with the electrical contact 160 of the socket 150 and the electrical contact 170 of the base 120, the cover 100 may reduce the likelihood of oxidation of the electrical contact 160 of the socket 150 and the electrical contact of the base 120. If oxidation is reduced, replacement of the lamp 130 and the socket 150 may be less frequent, resulting in reduced life cycle maintenance costs.

As the cover 100 shields liquids from coming in contact with the electrical contact 160 of the socket 150 and the electrical contact 170 of the base 120, the cover 100 may reduce the likelihood of arcing among the electrical contact 160 of the socket 150 and the electrical contact of the base 120. If arcing is reduced, replacement of the lamp 130 and the socket 150 may be less frequent, resulting in reduced life cycle maintenance costs. Moreover, other power source component failures may be prevented, resulting in reduced life cycle maintenance costs.

As the cover 100 shields liquids from coming in contact with the electrical contact 160 of the socket 150 and the electrical contact 170 of the base 120, the cover 100 may reduce the likelihood of fire being started between the electrical contact 160 of the socket 150 and the electrical contact of the base 120. If a source of fire is reduced, replacement of the system may be less frequent, resulting in reduced life cycle maintenance costs. Moreover, other safety benefits may be achieved.

Figure 2:
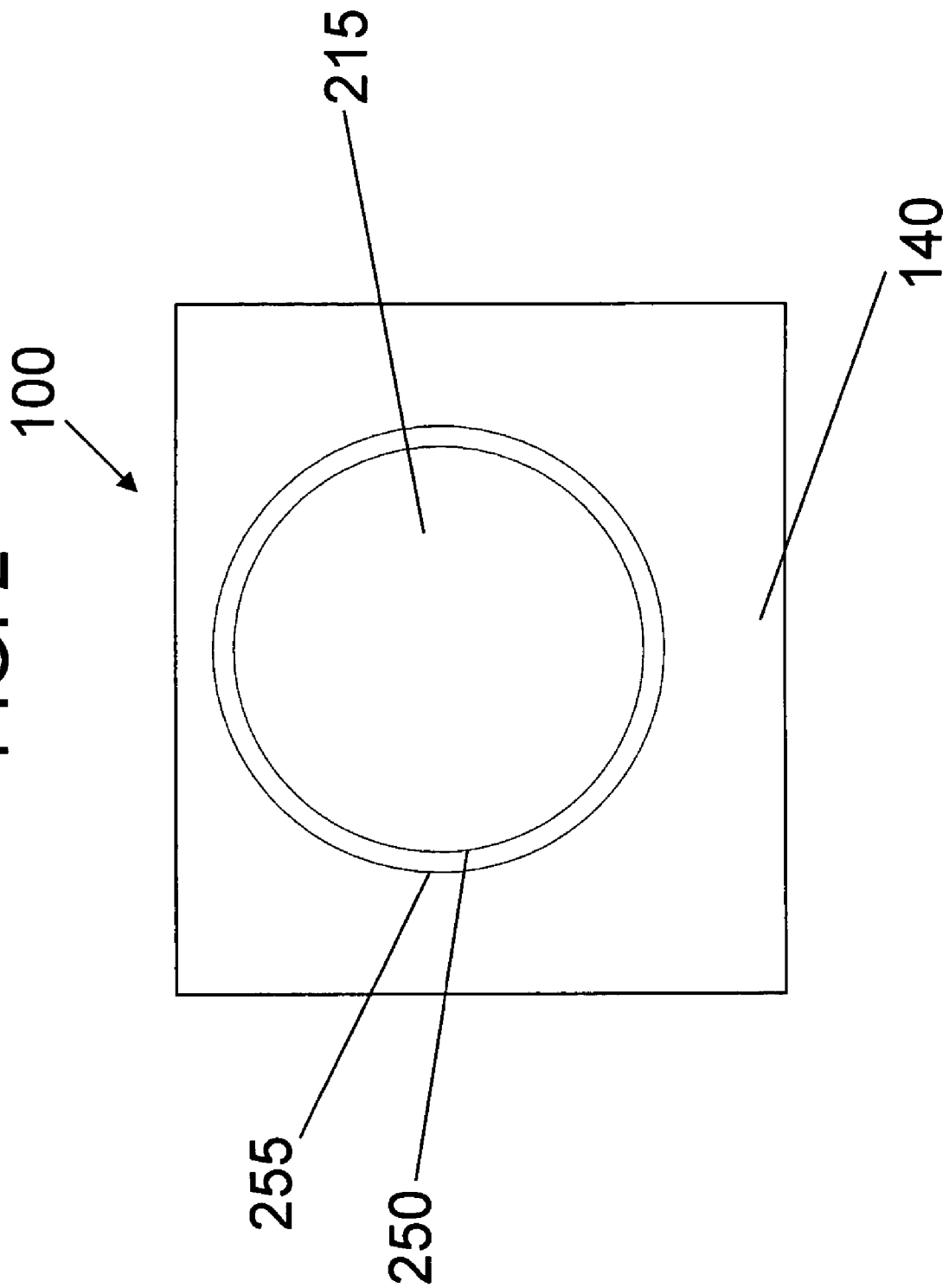
FIG. 2 is a plan view of a cover in accordance with the invention.

Referring now to FIG. 2, there is shown a plan view of the cover 100 in accordance with the invention. The shape and dimensions of the opening 215 may be chosen based on the geometry of the lamp 130 and the fixture 175. The cover 100 may have an inner surface 250 and an outer surface 255. The thickness of the material between the inner surface 250 and the outer surface 255 may be $1/16^{th}$ of an inch. The thickness may be uniform throughout the cover 100 or vary throughout the cover 100. The thickness may depend on the application and environment to which it will be subject.

The opening 215 of the first section 110 is adapted to receive the base 120 of the lamp 130. The inner surface 250 of the cover 100 at the first section 110 is adapted dimensionally to encompass and be at least slightly larger than an outer cross section of the base 120 of the lamp 130 when the first section 110 receives the base 120.

The cover 100 may include a ridge (not shown) for reducing the surface area in contact between the inner surface of the cover 100 at the first section 110 and the base 120. The ridge may protrude inward approximately $1/16^{th}$ of an inch from the inner surface of the cover 100 at the first section 110. The ridge may circumscribe the inner surface of the cover 100 at the first section 110. The ridge my be located $1/8^{th}$ of an inch from the opening 215 of the first section 110. The ridge may be $1/16^{th}$ of an inch thick. The dimensions of the ridge may be varied dependent on the amount of surface area desired to be in contact between the inner surface of the cover 100 at the first section 110 and the base 120.

The inner surface 250 of the first section 110 may have an opening 215 that is circular and is at least approximately 0.75 inches in diameter. The opening 215 is not required to have a diameter of at least approximately 0.75 inches in diameter.

The inner surface 250 of the cover 100 at the first section 100 is not required to be at least slightly larger than an outer cross section of the base 120 of the lamp 130 at all times. The cover 100 may be elastic. If the cover 100 is elastic the inner surface of the cover 100 at the first section 100 may be dimensionally equivalent or smaller than an outer cross section of the base 120 of the lamp. The first section 110 may be stretched to enable the inner surface 250 of the cover 100 at the first section 110 to accommodate the base 120. The opening 215 is not required to be circular. The shape of the opening 215 may be chosen based on the geometry of the base 120 of the lamp 130.

Figure 3:
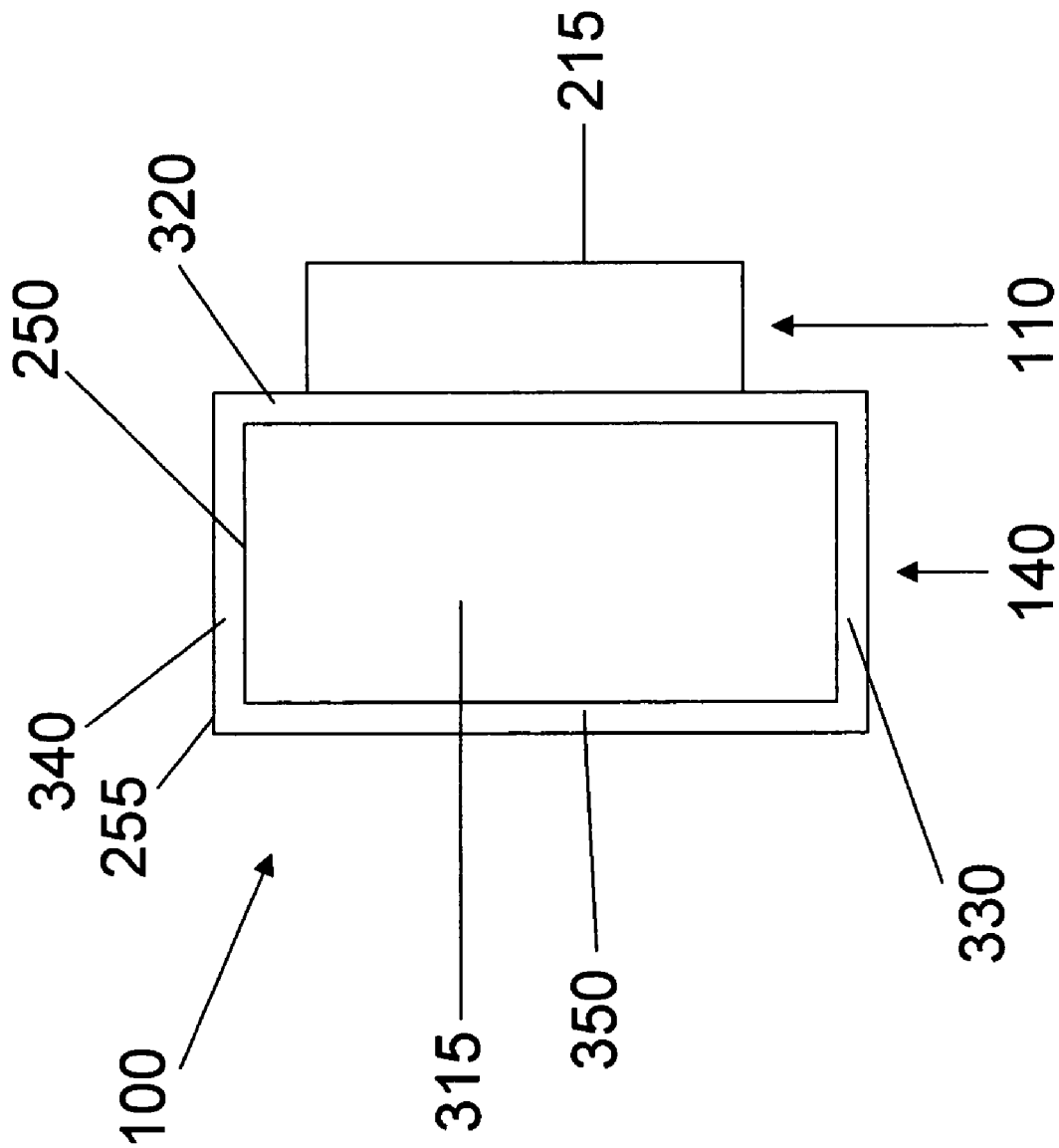
FIG. 3 is an elevation view of the bottom of the cover of FIG. 2.

Referring now to FIG. 3, there is shown an elevation view of the cover 100 of FIG. 1 as seen from the housing 180. An opening 315 of the second section 140 is adapted to receive the socket 150 of the fixture 175. The inner surface 250 of the cover 100 at the second section 140 is adapted dimensionally to encompass and be at least slightly larger than an outer cross section of the socket 150 when the opening 315 of the second section 140 receives the socket 150. The shape of the opening 315 may be chosen based on the geometry of the socket 150 of the fixture 175.

The opening 315 of the second section 140 may have a generally rectangular cross section. The opening 315 may be defined by a first wall 320 that is adjacent to the first section 110, a second wall 350 that is opposite to the first wall 320, a third wall 330 and fourth wall 340 that complete the rectangular cross section. The dimension of the opening 315 along the inner surface 250 of the first wall 320 and the second wall 350 may be at least approximately $1 3/8^{th}$ inches.

The dimension of the opening 315 along the inner surface 250 of the third wall 330 and the fourth wall 340 may be at least approximately $7/16^{th}$ inches. The dimension of the length of the first section 110, measured from the outer surface 255 at the first wall 320 to the opening 215 may be at least $3/16^{th}$ inches.

If the cover is elastic then the inner surface 250 of the cover 100 at the second section 140 may be dimensionally equivalent or smaller than an outer cross section of the socket 150 of the fixture 175. If so, the second section 140 may be stretched to enable the inner surface 250 of the cover 100 at the second section 140 to accommodate the socket 150.

Figure 4:
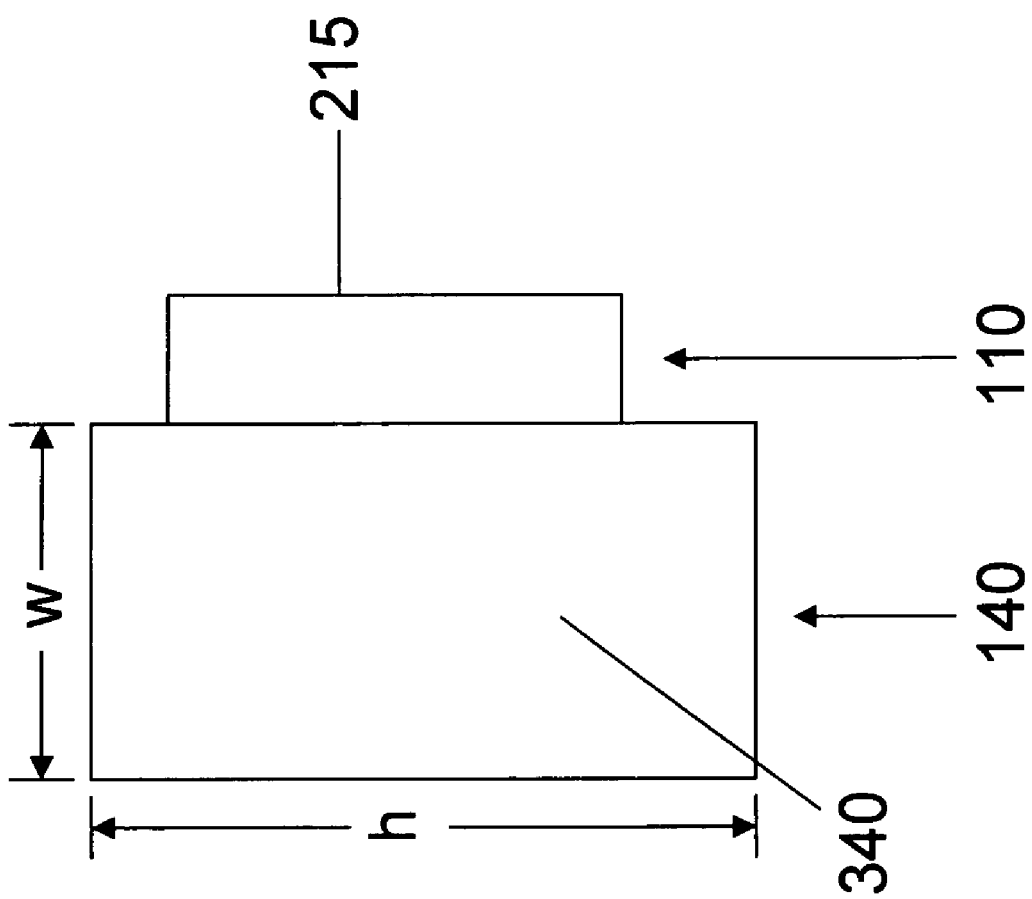
FIG. 4 is a perspective view of the cover of FIG. 2.

Referring now to FIG. 4, there is shown a perspective view of the cover 100 viewed from the same perspective of FIG. 1. The fourth wall 340 may have a height h of at least approximately $1 1/16^{th}$ inches. The fourth wall 340 may have a width w of at least approximately ½ inch. The height h and the width w of the fourth wall 340 are not required to be at least approximately $1 1/16^{th}$ inches and ½ inches, respectively. The dimensions and shape of the fourth wall may be modified to shield the socket, the electrical leads of the socket. Moreover, the dimensions of the fourth wall may be modified to accommodate the flange or abut the housing.

Figure 5:
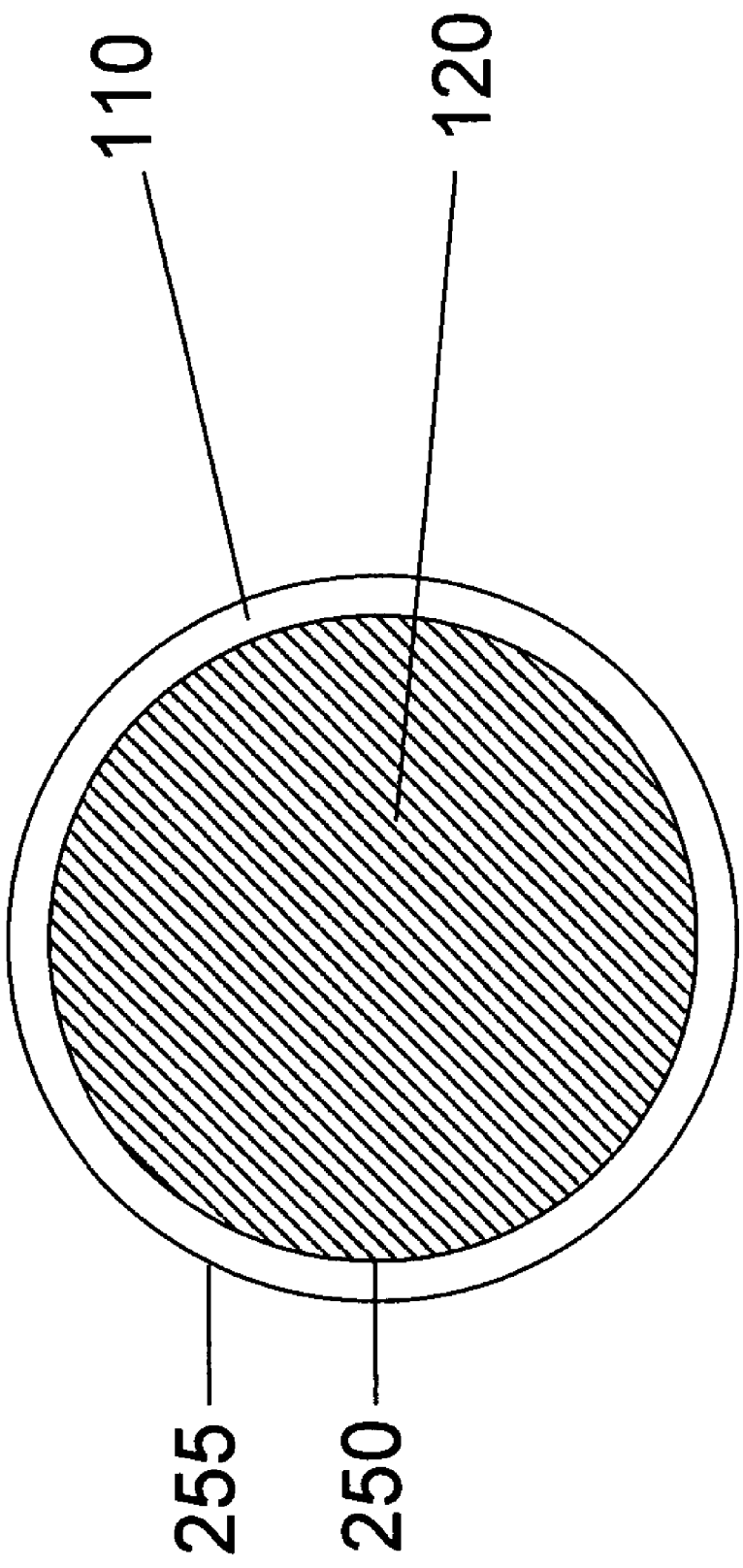
FIG. 5 is partial sectional view A—A of the system of FIG. 1.

Referring now to FIG. 5, there is shown a partial sectional view A—A of the system of FIG. 1. In this embodiment the first section 110 of the cover 100 is surrounding a full cross section of the base 120.

The cover 100 may have a cavity between the opening 215 of the first section 110 and the opening 315 of the second section 140. The cavity or hollow portion within the cover 100 may be large enough to accommodate the assembly of the cover 100 with the base 120, the flange 185, the socket 150, the fastener 1010, the electrical contact 170 of the base, and the electrical contact 160 of the socket 150. The cavity is defined by the inner surface 250 of the cover 100. The inner surface 250 of the cover 100 may be electrically insulating.

Figure 6:
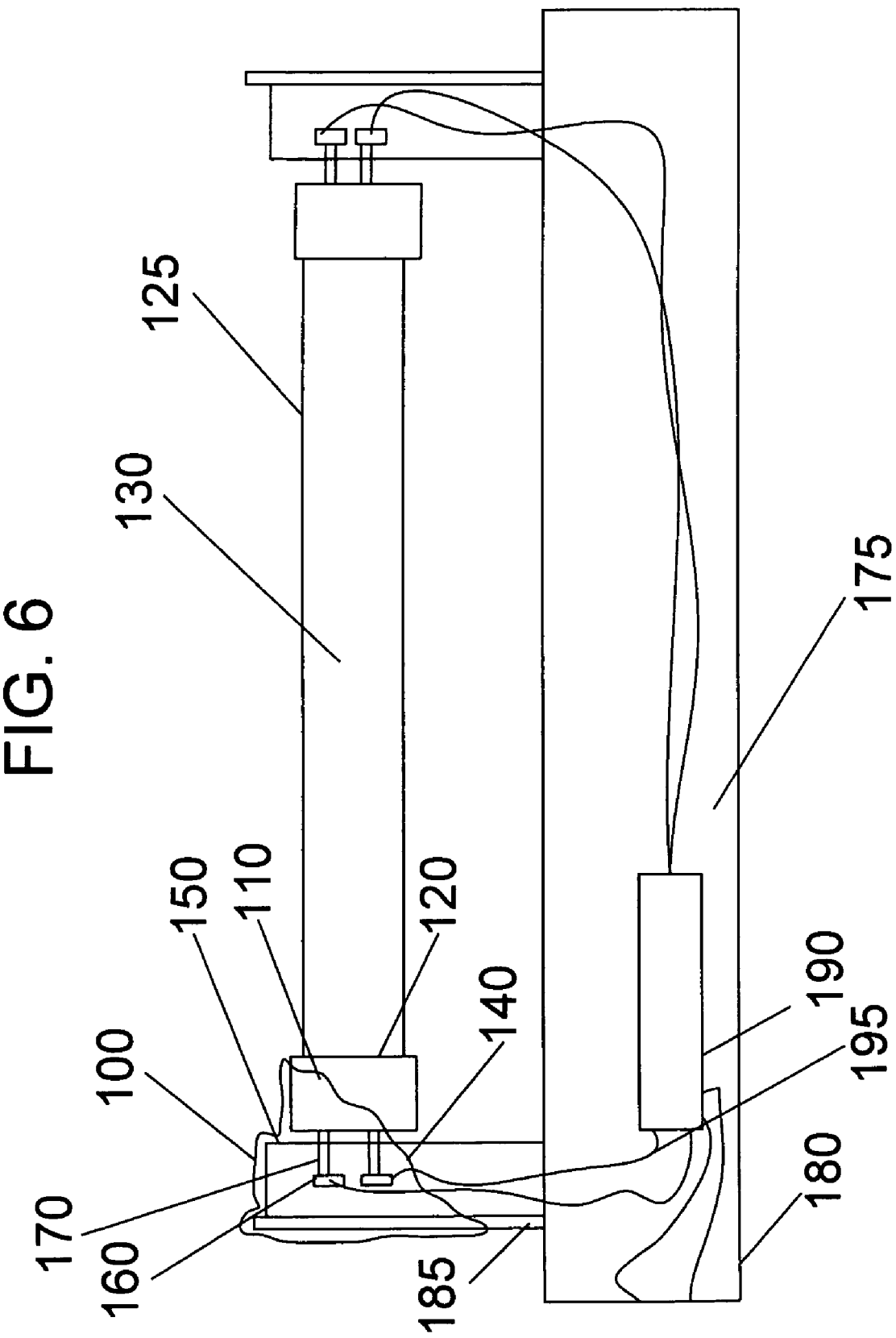
FIG. 6 is a perspective view of a system in accordance with the invention.

Referring now to FIG. 6, there is shown an alternate embodiment where the first section 110 partially surrounds the base 120. In this embodiment, the cover 100, the base 120, and the socket 150 may partially enclose the electrical contact 160 of the socket 150 and the electrical contact 170 of the base 120. Alternatively, the cover 100, the base 120 and the socket 150 may completely enclose the electrical contact 160 of the socket 150 and the electrical contact 170 of the base 120.

Figure 7:
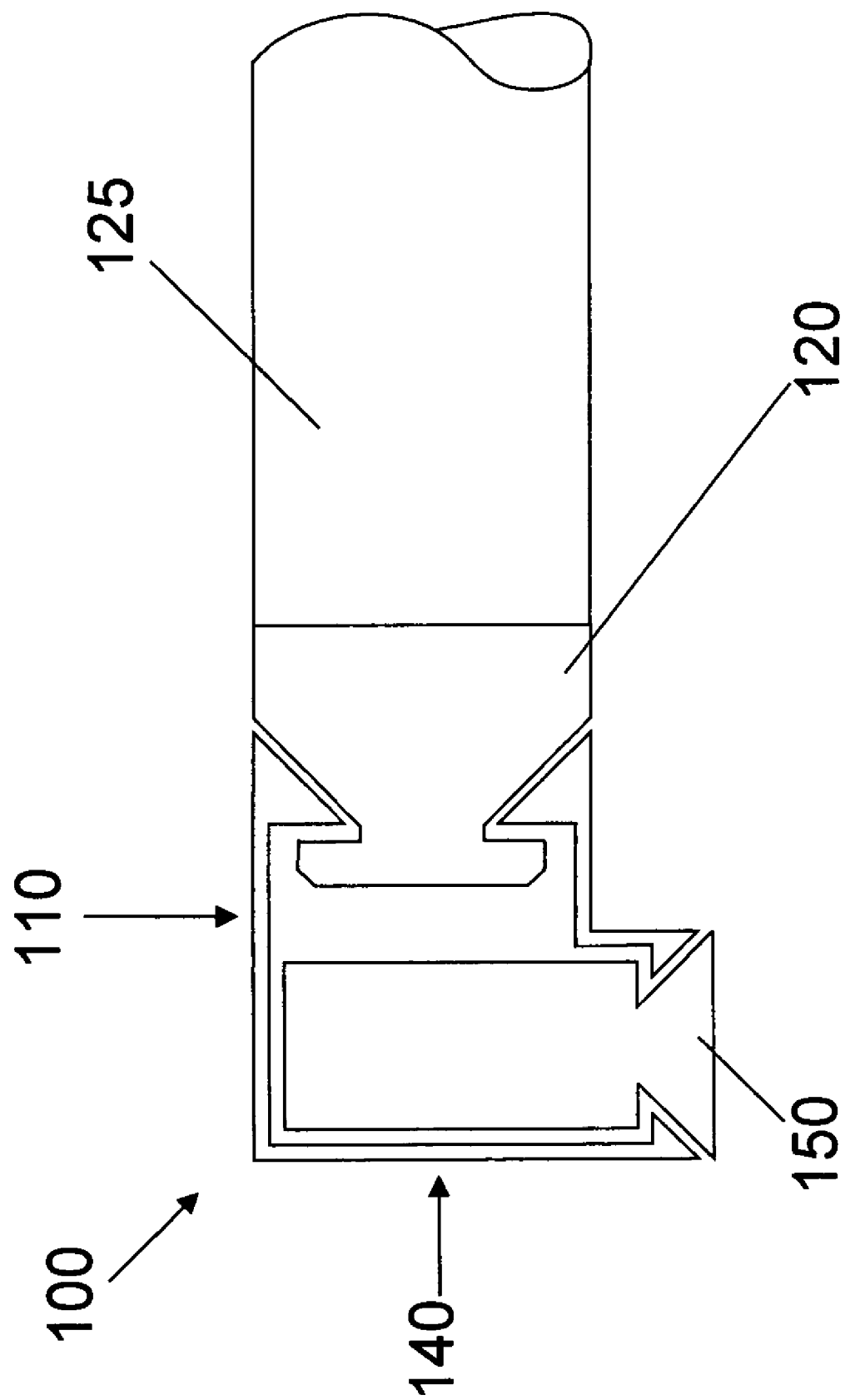
FIG. 7 is a first partial perspective view of the system of FIG. 6.

Referring now to FIG. 7, there is shown an alternate embodiment where the first section 110 at least partially interlocks with the base 120. Additionally, the second section 140 may at least partially interlock with the socket 150.

Figure 8:
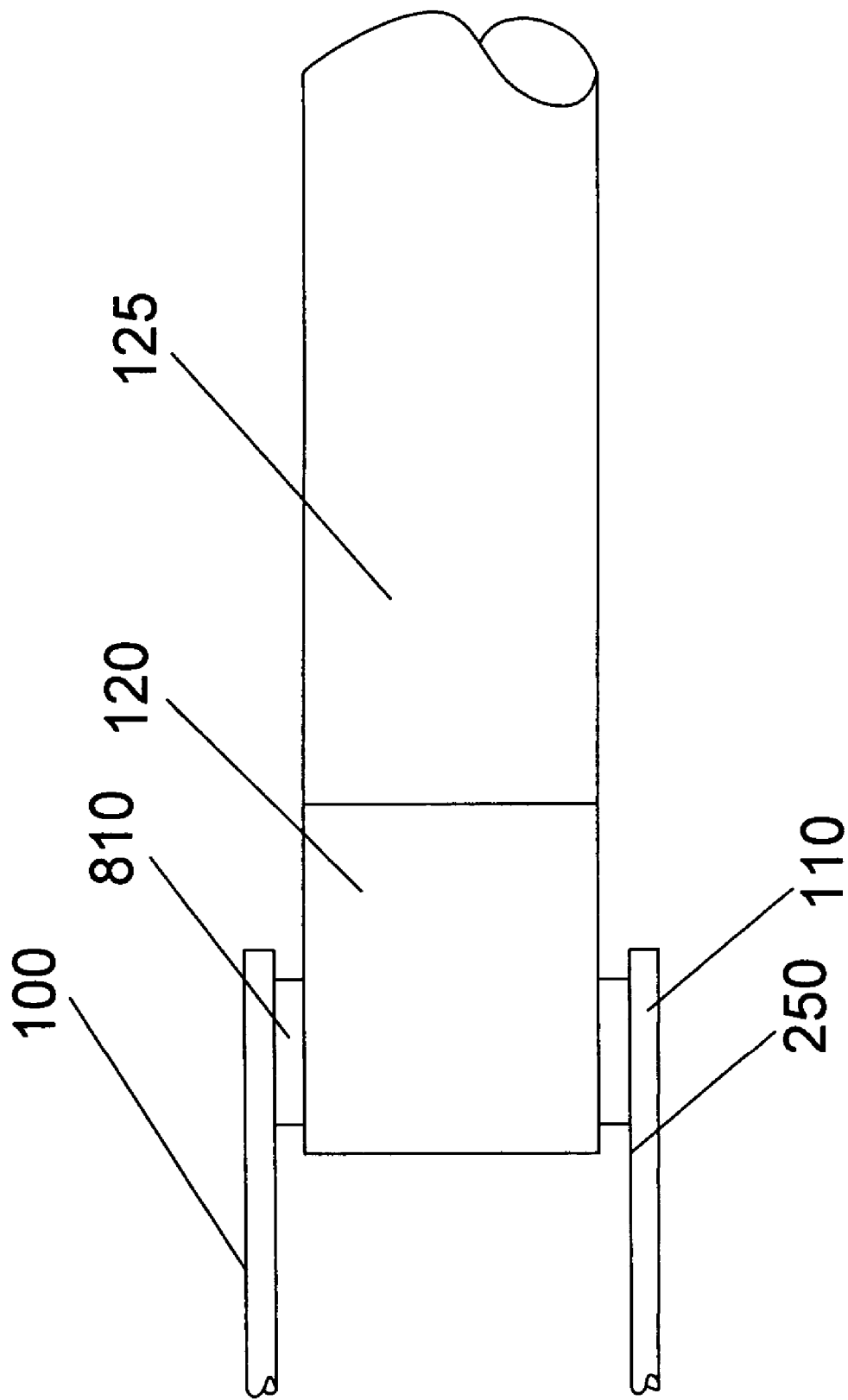
FIG. 8 is a second partial perspective view of the system of FIG. 6.

Referring now to FIG. 8, there is shown an alternate embodiment where the first section 110 at least partially seals to the base 120. Additionally, the second section 140 may at least partially seal to the socket 150. The seal 810 may be a glue, cement, RTV, or silicone that is suitable for exposure to temperature and or light. Moreover, the seal 810 may be a gasket, bushing, or o-ring that is compressed between the inner surface 250 of the cover 100 at the first section 110 and the base 120. The gasket, bushing or o-ring may be coated by silicon liquid or gel for better sealing or ease of assembly. The seal 810 may be a tight interference fit.

Figure 9:
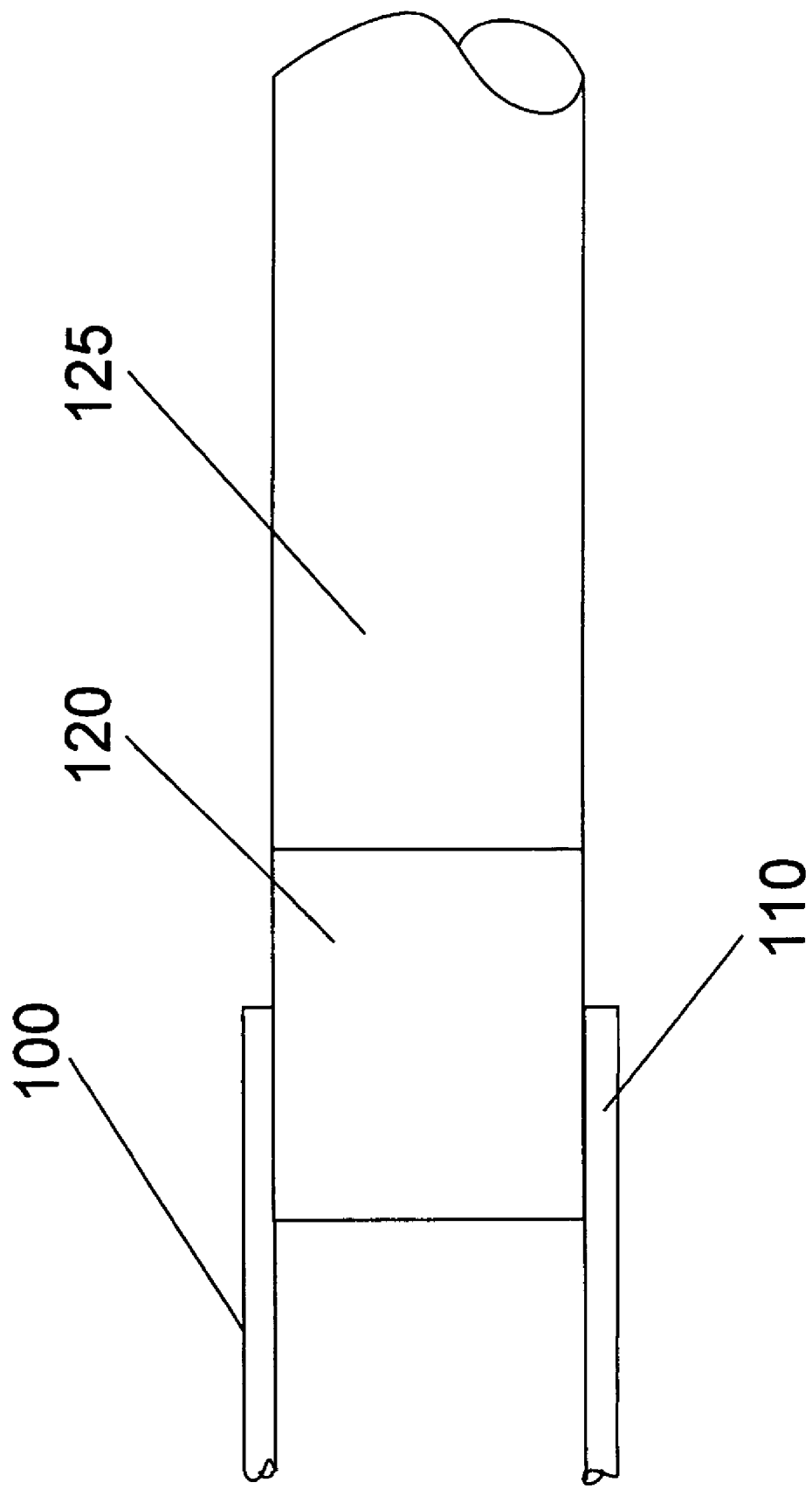
FIG. 9 is a third partial perspective view of the system of FIG. 6.

Referring now to FIG. 9, there is shown an alternate embodiment where the first section 110 at least partially abut the base 120. Additionally, the second section 140 may at least partially abut to the socket 150.

Figure 10:
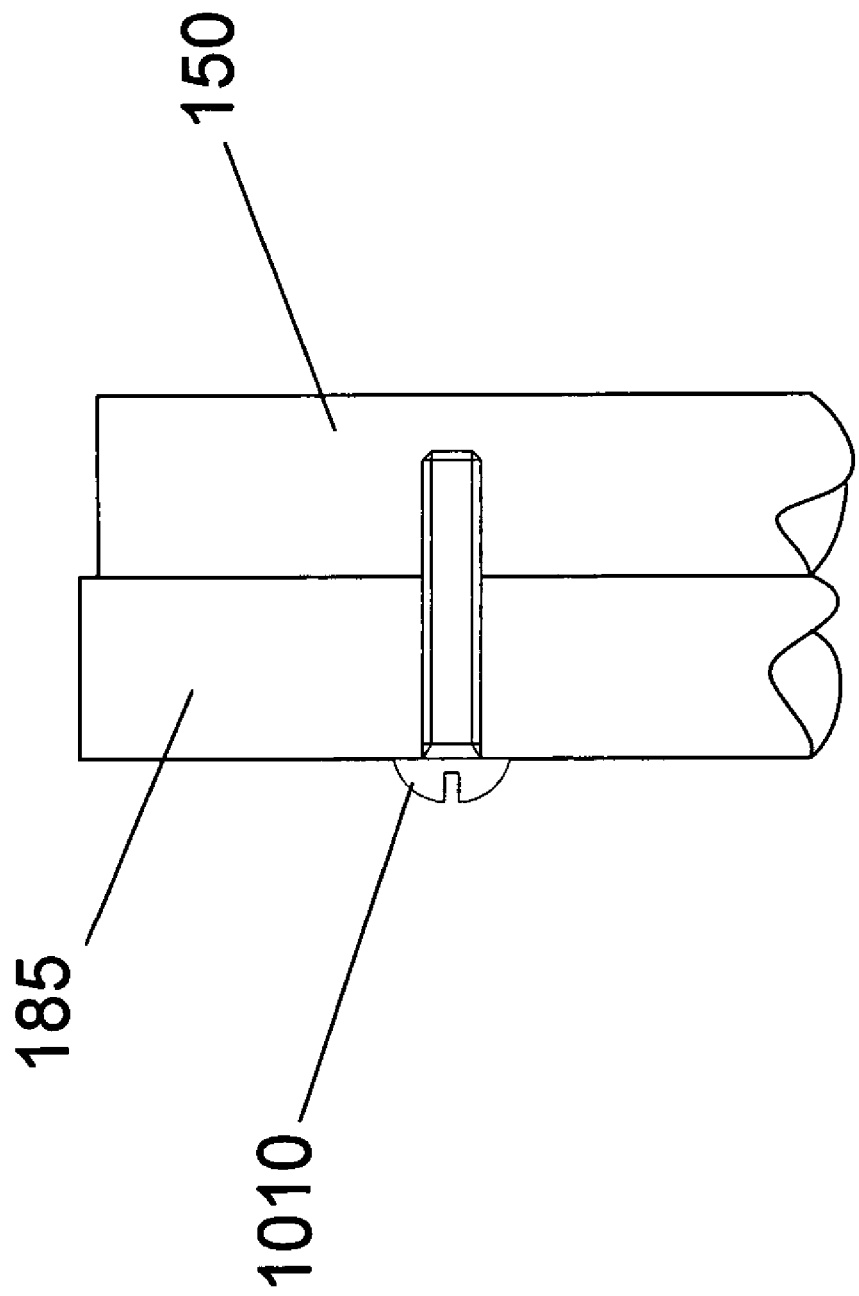
FIG. 10 is a partial perspective view of a socket and a flange in accordance with the invention.
Figure 11:
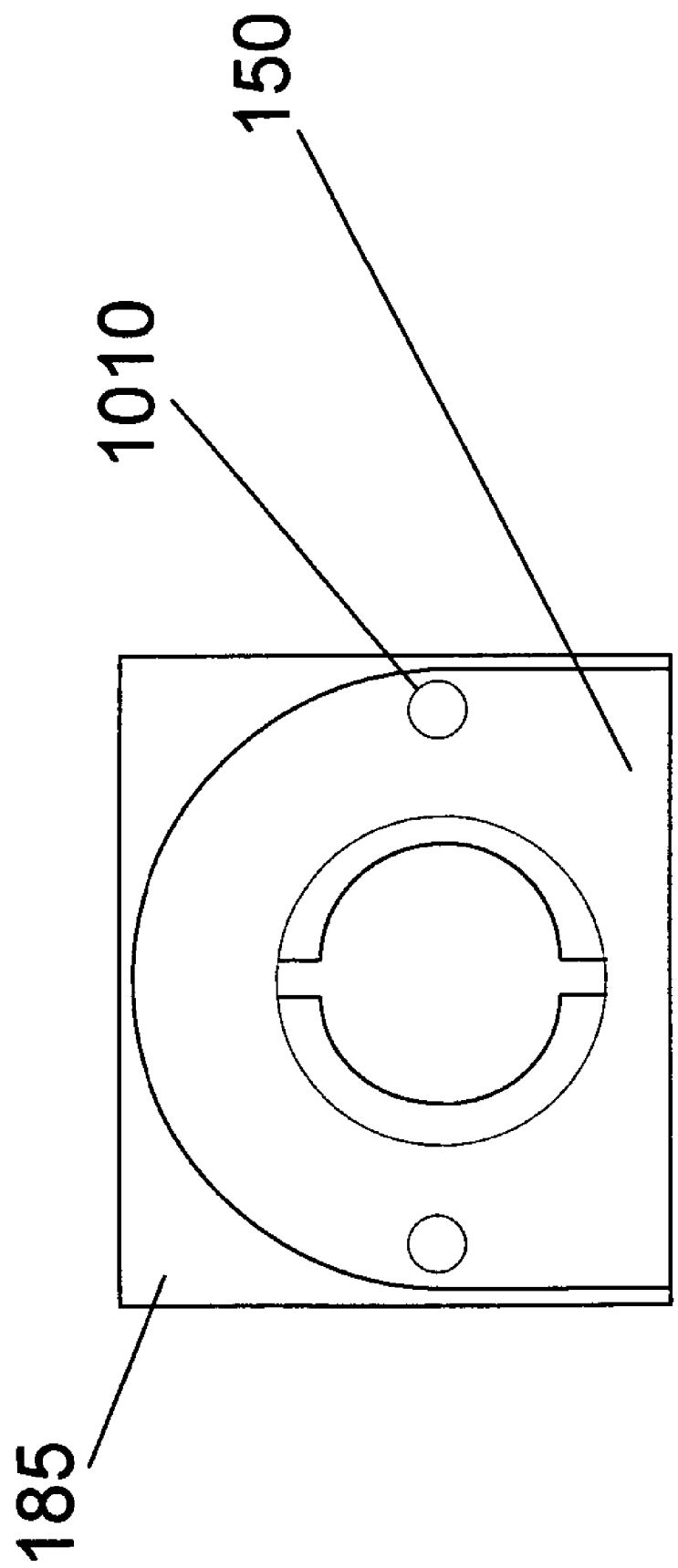
FIG. 11 is a partial plan view of the socket and the flange of FIG. 10.

Referring now to FIG. 10 and FIG. 11, there is shown the socket 150 attached to the flange 185. The socket 150 maybe fastened to the flange 185 using fasteners 1010. The fasteners 1010 may be a screw, bolt, rivet, pin. The head of the fasteners 1010 may be any common head, for example, square, hex, or flat. Alternatively, the socket 150 may be glued or cemented with an appropriate adhesive to the flange 185. The choice of adhesives would depend on the environment that the assembly would operate in, the load it would need to support, and the material of the flange 185 and the socket 140.

Figure 12:
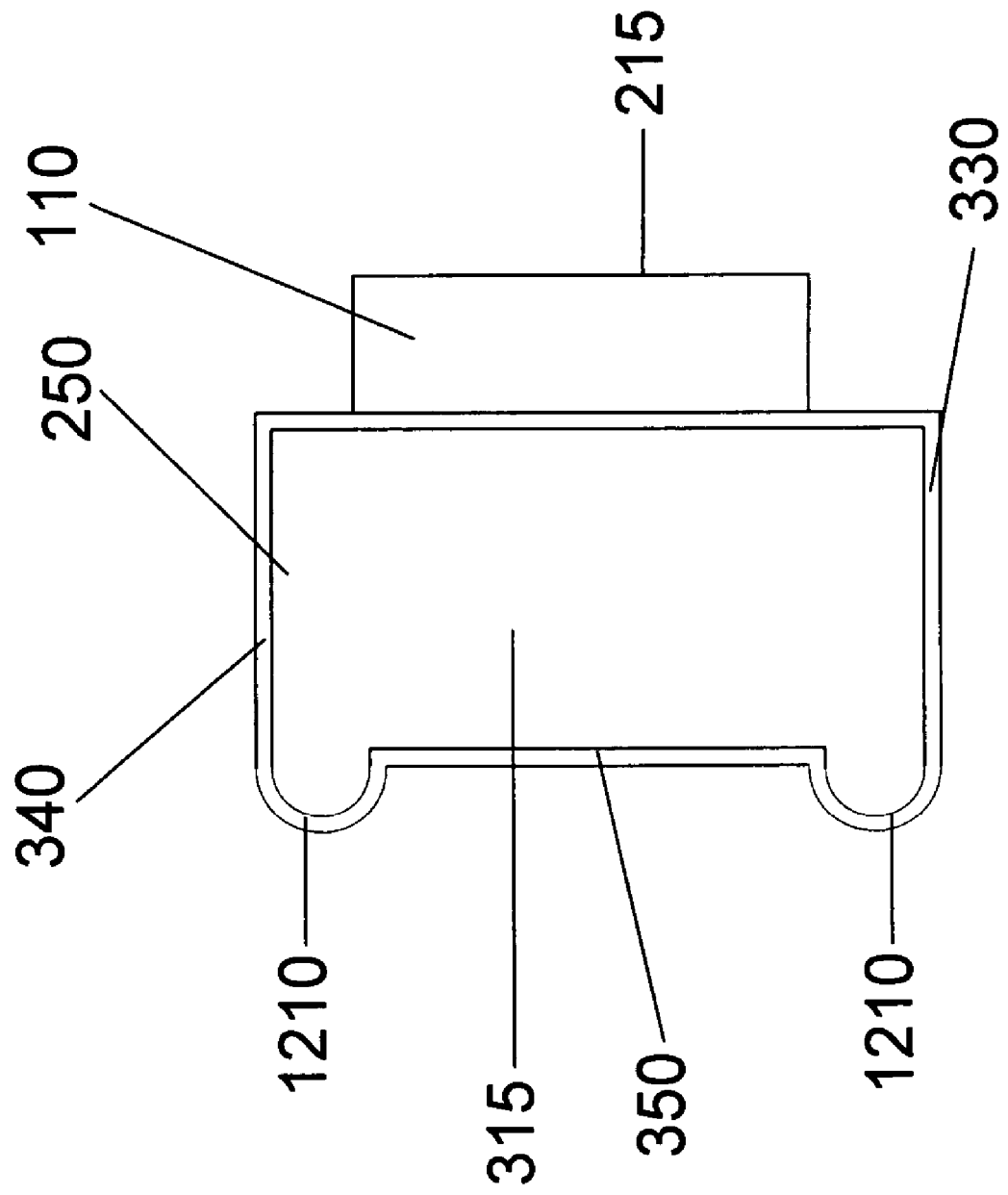
FIG. 12 is an elevation view of the cover in accordance with the invention.

Referring now to FIG. 12, there is shown an elevation view of a cover 100 in accordance with the invention. This view is from the direction of the housing 180. This figure shows an alternate embodiment of the cover 100 as previously shown in FIG. 3. The second wall 350 may have end sections 1210 that are perpendicular to the third wall 330 and the fourth wall 340. The end sections 1210 may be provided to accommodate the fasteners 1010 as shown in FIG. 10 and FIG. 11. The end sections 1210 may take the form of a semicircle. A semicircle end section accommodates a round headed fastener. The diameter dimension of the end sections 1210 may be 0.25 inches. The shape of the end sections 1210 may be chosen to accommodate the shape and dimensions of the fasteners. Should the head of the fasteners be flush with the flange, the second wall 350 may be flat without specially shaped end sections 1210.

Figure 13:
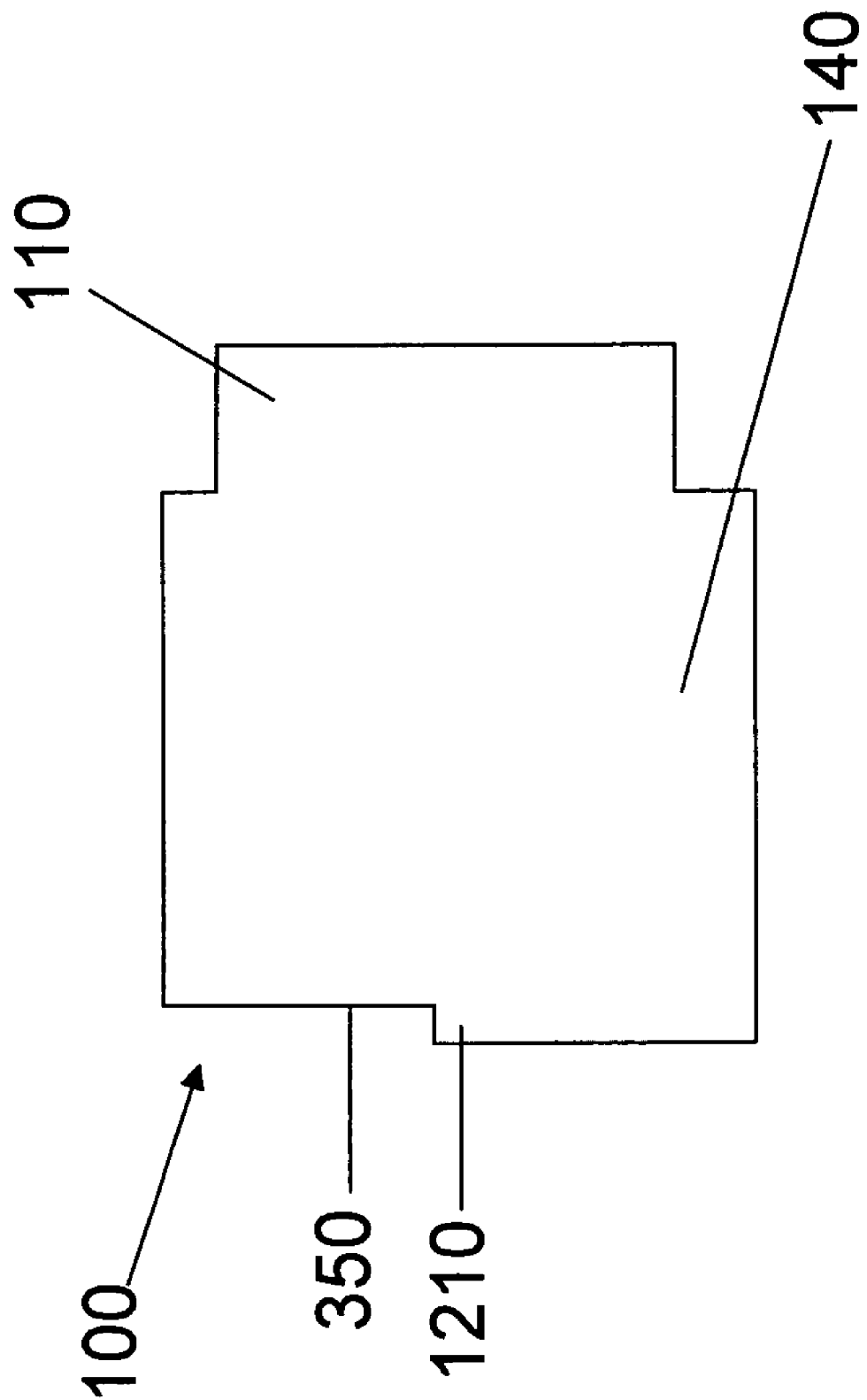
FIG. 13 is a perspective view of a cover in accordance with the invention.

Referring now to FIG. 13, there is shown a perspective view of the cover 100. In this view is shown the embodiment that includes the end sections 1210 feature. The end sections 1210 may be a feature that is along the whole height of the second wall 350, $3/4^{th}$ of the height of the second wall 350, or $1/4^{th}$ of the height of the second wall. The end sections 1210 feature may extend ½ the height of the second wall 350. The end sections 1210 may be of different shape and dimension based on the dimensions of the flange, socket and fasteners.

Figure 14:
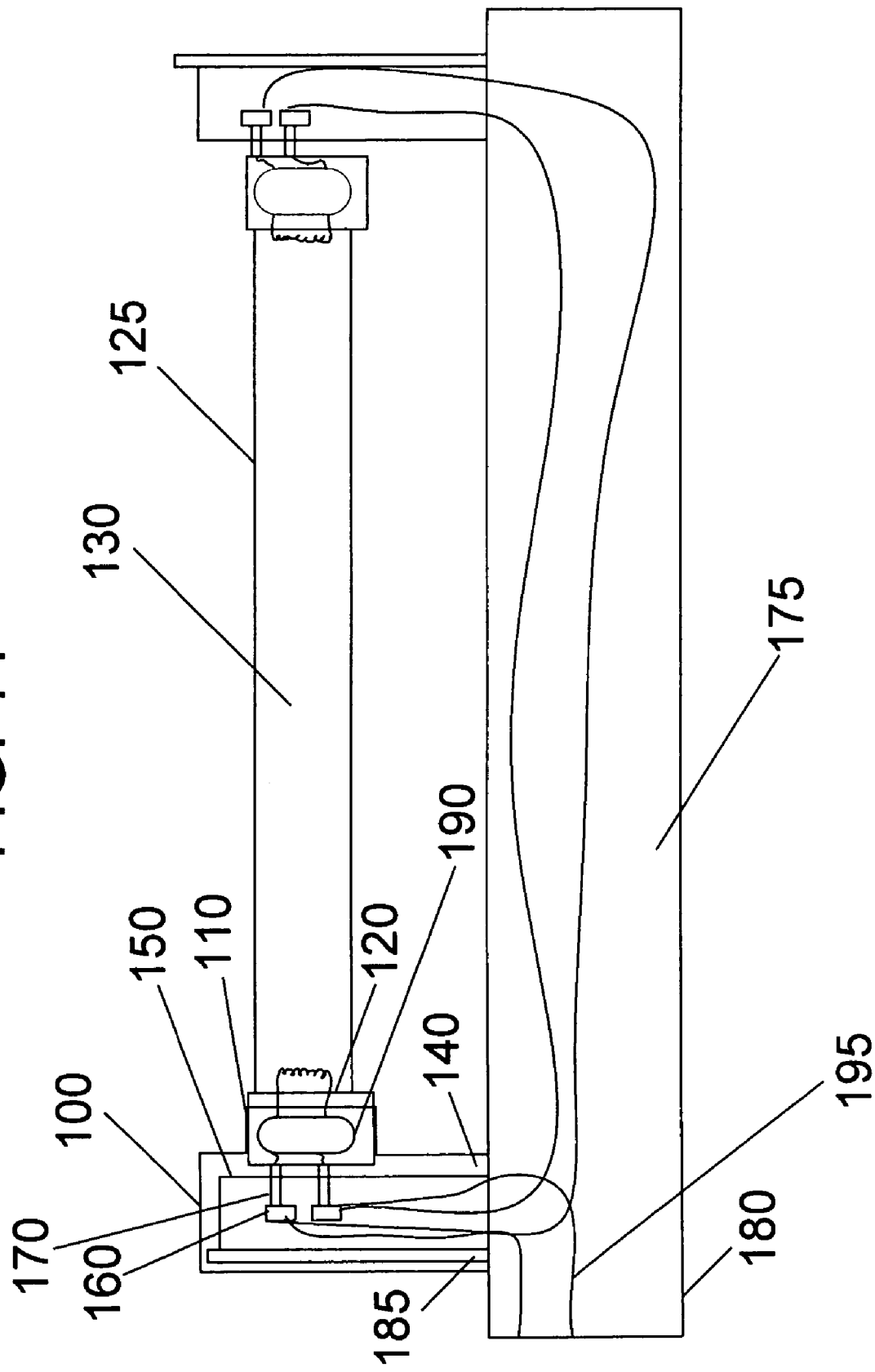
FIG. 14 is a perspective view of a system in accordance with the invention.

Referring now to FIG. 14, there is shown an alternate embodiment where there is a remote power source that is electrically connected via wiring 195 to the electrical contact 160 of the socket 150. The electrical contact 160 of the socket is electrically connected to the electrical contact 170 of the base 120. The electrical contact 170 of the base 120 is electrically connected to the power supply 190. The remote power source provides power to the power supply 190. In this embodiment the power supply 190 is located within the base 120. As shown, the power supply 190 provides electric power directly to the electrode 105 of the base 120.

For assembling the environmentally resistant germicidal system, the following steps may be performed: The first section 110 may be positioned at least partially around the base 120. The second section 140 may be positioned at least partially around the socket 150. The base 120 may be positioned to engage the socket 150 wherein the socket 150 provides mechanical support to the base 120 and the electrical contact 170 of the base 120 electrically contacts the electrical contact 160 of the socket 150.

Alternatively, a sealing adhesive may be applied both between the first section 110 and the base 120 and between the second section 140 and the socket 150. Moreover, a gasket or o-ring may be installed during the positioning of the both the first section 110 and the base 120 and between the second section 140 and the socket 150.

Although shown implemented with a double ended lamp, the invention may be implemented with any lamp. A germicidal lamp as used herein refers to any lamp enclosing a vaporizable material that may kill bioaerosols including, but not limited to, germs, viruses, molds, yeasts, and bacteria. These germicidal lamps may take any shape, for example, a toroid or single ended.

With regard to assembling the environmentally resistant germicidal system, additional and fewer steps may be taken, and the steps as shown may be combined or further refined to achieve the methods described herein.

Although exemplary embodiments of the present invention have been shown and described, it will be apparent to those having ordinary skill in the art that a number of changes, modifications, or alterations to the invention as described herein may be made, none of which depart from the spirit of the present invention. All such changes, modifications and alterations should therefore be seen as within the scope of the present invention.

It is claimed:

1. An environmentally resistant lamp system comprising:

a fixture having
  a housing providing mechanical support
  a socket attached to the housing comprising an electrical contact electrically connected to a power supply,
a lamp having
  a single-walled envelope
  a base attached to the envelope
  a vaporizable material sealed within the envelope
  at least one electrode disposed within the envelope
  an electrical contact attached to the base, electrically connected to the electrode
  whereby the lamp is mechanically supported by the socket and the electrical contact of the lamp electrically connects to the electrical contact of the socket,
a cover having
  a material resistant to at least one of dripping liquid, light splashing of liquid, and condensation
  a first section at least partially surrounding the base
  a second section at least partially surrounding the socket
  an inner surface at least partially surrounding the electrical contact of the socket and the electrical contact of the base
  an outer surface shielding the electrical contact of the socket and the electrical contact of the base
wherein the first section at least partially abuts the base and the second section at least partially abuts the socket.

2. An environmentally resistant lamp system comprising:

a fixture having
  a housing providing mechanical support
  a socket attached to the housing comprising an electrical contact electrically connected to a power supply,
a lamp having
  a single-walled envelope
  a base attached to the envelope
  a vaporizable material sealed within the envelope
  at least one electrode disposed within the envelope
  an electrical contact attached to the base, electrically connected to the electrode
  whereby the lamp is mechanically supported by the socket and the electrical contact of the lamp electrically connects to the electrical contact of the socket,
a cover having
  a material resistant to at least one of dripping liquid, light splashing of liquid, and condensation
  a first section at least partially surrounding the base
  a second section at least partially surrounding the socket
  an inner surface at least partially surrounding the electrical contact of the socket and the electrical contact of the base
  an outer surface shielding the electrical contact of the socket and the electrical contact of the base
wherein the first section at least partially interlocks with the base and the second section at least partially interlocks with the socket.

3. An environmentally resistant lamp system comprising:

a fixture having
  a housing providing mechanical support
  a socket attached to the housing comprising an electrical contact electrically connected to a power supply,
a lamp having
  a single-walled envelope
  a base attached to the envelope
  a vaporizable material sealed within the envelope
  at least one electrode disposed within the envelope
  an electrical contact attached to the base, electrically connected to the electrode
  whereby the lamp is mechanically supported by the socket and the electrical contact of the lamp electrically connects to the electrical contact of the socket,
a cover having
  a material resistant to at least one of dripping liquid, light splashing of liquid, and condensation
  a first section at least partially surrounding the base
  a second section at least partially surrounding the socket
  an inner surface at least partially surrounding the electrical contact of the socket and the electrical contact of the base
  an outer surface shielding the electrical contact of the socket and the electrical contact of the base
wherein the first section at least partially seals to the base and the second section at least partially seals to the socket.

4. An environmentally resistant lamp system comprising:

a fixture having
  a housing providing mechanical support
  a socket attached to the housing comprising an electrical contact electrically connected to a power supply,
a lamp having
  a single-walled envelope
  a base attached to the envelope
  a vaporizable material sealed within the envelope
  at least one electrode disposed within the envelope
  an electrical contact attached to the base, electrically connected to the electrode
  whereby the lamp is mechanically supported by the socket and the electrical contact of the lamp electrically connects to the electrical contact of the socket,
a cover having
  a material resistant to at least one of dripping liquid, light splashing of liquid, and condensation
  a first section at least partially surrounding the base
  a second section at least partially surrounding the socket
  an inner surface at least partially surrounding the electrical contact of the socket and the electrical contact of the base
  an outer surface shielding the electrical contact of the socket and the electrical contact of the base
wherein the first section at least partially interlocks with the base and the second section at least partially interlocks with the flange.

5. An environmentally resistant lamp system comprising:
a fixture having
  a housing providing mechanical support
  a socket attached to the housing comprising an electrical contact electrically connected to a power supply,
a lamp having
  a single-walled envelope
  a base attached to the envelope
  a vaporizable material sealed within the envelope
  at least one electrode disposed within the envelope
  an electrical contact attached to the base, electrically connected to the electrode
  whereby the lamp is mechanically supported by the socket and the electrical contact of the lamp electrically connects to the electrical contact of the socket,
a cover having
  a material resistant to at least one of dripping liquid, light splashing of liquid, and condensation
  a first section at least partially surrounding the base
  a second section at least partially surrounding the socket
  an inner surface at least partially surrounding the electrical contact of the socket and the electrical contact of the base
  an outer surface shielding the electrical contact of the socket and the electrical contact of the base
wherein the first section at least partially seals to the base and the second section at least partially seals the flange.

6. An environmentally resistant lamp system comprising:
a fixture having
  a housing providing mechanical support
  a socket attached to the housing comprising an electrical contact electrically connected to a power supply,
a lamp having
  a single-walled envelope
  a base attached to the envelope
  a vaporizable material sealed within the envelope
  at least one electrode disposed within the envelope
  an electrical contact attached to the base, electrically connected to the electrode
  whereby the lamp is mechanically supported by the socket and the electrical contact of the lamp electrically connects to the electrical contact of the socket,
a cover having
  a material resistant to at least one of dripping liquid, light splashing of liquid, and condensation
  a first section at least partially surrounding the base
  a second section at least partially surrounding the socket
  an inner surface at least partially surrounding the electrical contact of the socket and the electrical contact of the base
  an outer surface shielding the electrical contact of the socket and the electrical contact of the base
wherein the power supply is mounted to the housing, the first section at least partially abuts the base, the second section at least partially abuts the socket, the liquid is water, and the tube emits ultraviolet light.

7. An environmentally resistant cover for a germicidal system comprising:
a material resistant to at least one of-dripping liquid, light splashing of liquid, light spraying of liquid and condensation
a first section having
  an opening adapted to receive a base of an electric discharge lamp
  an inner surface adapted dimensionally to encompass and be at least slightly larger than an outer cross section of the base when the first section receives the base
a second section having
  an opening adapted to receive a socket of an electric discharge lamp fixture
  an inner surface adapted dimensionally to encompass and be at least slightly larger than an outer cross section of the socket when the second section receives the socket
wherein the cover is adapted to, when the cover receives the base and the socket, shield and at least partially enclose both an electrical contact of the base and an electrical contact of the socket from at least one of dripping liquid, light splashing of liquid, light spraying of liquid and condensation
wherein a cross section of the inner surface of the first section is further adapted to fit with an outer cross section of the base, and a cross section of the inner surface of the second section is further adapted to fit with at least part of an outer cross section of the socket.

8. An environmentally resistant cover for a germicidal system comprising:
a material resistant to at least one of-dripping liquid, light splashing of liquid, light spraying of liquid and condensation
a first section having
  an opening adapted to receive a base of an electric discharge lamp
  an inner surface adapted dimensionally to encompass and be at least slightly larger than an outer cross section of the base when the first section receives the base
a second section having
  an opening adapted to receive a socket of an electric discharge lamp fixture
  an inner surface adapted dimensionally to encompass and be at least slightly larger than an outer cross section of the socket when the second section receives the socket
wherein the cover is adapted to, when the cover receives the base and the socket, shield and at least partially enclose both an electrical contact of the base and an electrical contact of the socket from at least one of dripping liquid, light splashing of liquid, light spraying of liquid and condensation
wherein a cross section of the inner surface of the first section is further adapted to interlock with an outer cross section of the base, and a cross section of the inner surface of the second section is further adapted to interlock with at least part of an outer cross section of the socket.

9. An environmentally resistant cover for a germicidal system comprising:
a material resistant to at least one of-dripping liquid, light splashing of liquid, light spraying of liquid and condensation
a first section having
  an opening adapted to receive a base of an electric discharge lamp
  an inner surface adapted dimensionally to encompass and be at least slightly larger than an outer cross section of the base when the first section receives the base a second section having
- an opening adapted to receive a socket of an electric discharge lamp fixture
- an inner surface adapted dimensionally to encompass and be at least slightly larger than an outer cross section of the socket when the second section receives the socket
- wherein the cover is adapted to, when the cover receives the base and the socket, shield and at least partially enclose both an electrical contact of the base and an electrical contact of the socket from at least one of dripping liquid, light splashing of liquid, light spraying of liquid and condensation
- wherein a cross section of the inner surface of the first section is further adapted to seal to an outer cross section of the base, and a cross section of the inner surface of the second section is further adapted to seal to at least part of an outer cross section of the socket.

10. An environmentally resistant cover for a germicidal system comprising:
- a material resistant to at least one of-dripping liquid, light splashing of liquid, light spraying of liquid and condensation
- a first section having
  - an opening adapted to receive a base of an electric discharge lamp
  - an inner surface adapted dimensionally to encompass and be at least slightly larger than an outer cross section of the base when the first section receives the base
- a second section having
  - an opening adapted to receive a socket of an electric discharge lamp fixture
  - an inner surface adapted dimensionally to encompass and be at least slightly larger than an outer cross section of the socket when the second section receives the socket
  - wherein the cover is adapted to, when the cover receives the base and the socket, shield and at least partially enclose both an electrical contact of the base and an electrical contact of the socket from at least one of dripping liquid, light splashing of liquid, light spraying of liquid and condensation
- wherein a cross section of the inner surface of the first section is further adapted to interlock with an outer cross section of the base, and a cross section of the opening of the second section is further adapted to interlock with a surface of a housing of the fixture.

11. An environmentally resistant cover for a germicidal system comprising:
- a material resistant to at least one of-dripping liquid, light splashing of liquid, light spraying of liquid and condensation
- a first section having
  - an opening adapted to receive a base of an electric discharge lamp
  - an inner surface adapted dimensionally to encompass and be at least slightly larger than an outer cross section of the base when the first section receives the base
- a second section having
  - an opening adapted to receive a socket of an electric discharge lamp fixture
  - an inner surface adapted dimensionally to encompass and be at least slightly larger than an outer cross section of the socket when the second section receives the socket
  - wherein the cover is adapted to, when the cover receives the base and the socket, shield and at least partially enclose both an electrical contact of the base and an electrical contact of the socket from at least one of dripping liquid, light splashing of liquid, light spraying of liquid and condensation
- wherein a cross section of the inner surface of the first section is further adapted to seal to an outer cross section of the base, and a cross section of the opening of the second section is further adapted to seal to a surface of the housing of the fixture.

12. An environmentally resistant cover for a germicidal system comprising:
- a material resistant to at least one of-dripping liquid, light splashing of liquid, light spraying of liquid and condensation
- a first section having
  - an opening adapted to receive a base of an electric discharge lamp
  - an inner surface adapted dimensionally to encompass and be at least slightly larger than an outer cross section of the base when the first section receives the base
- a second section having
  - an opening adapted to receive a socket of an electric discharge lamp fixture
  - an inner surface adapted dimensionally to encompass and be at least slightly larger than an outer cross section of the socket when the second section receives the socket
  - wherein the cover is adapted to, when the cover receives the base and the socket, shield and at least partially enclose both an electrical contact of the base and an electrical contact of the socket from at least one of dripping liquid, light splashing of liquid, light spraying of liquid and condensation
- wherein a cross section of the inner surface of the first section is adapted to at least partially interlock with an outer cross section of the base, a cross section of the inner surface of the second section is adapted to at least partially interlock with a surface of the housing of the fixture, the liquid is a mixture of water and oil, and the lamp is a germicidal lamp.

13. A process for providing environmental resistance to a germicidal system comprising:
- positioning a first section of a cover at least partially around a base of an electric discharge lamp,
- positioning a second section of the cover at least partially around a socket of a fixture,
- positioning an electrical contact of the base in electrical contact with an electrical contact of the socket,
- whereby the cover shields both the electrical contact of the base and the electrical contact of the socket from at least one of dripping liquid, light splashing liquid, and condensation
- wherein the cover at least partially abuts the base and the cover at least partially abuts the socket.

14. A process for providing environmental resistance to a germicidal system comprising:
- positioning a first section of a cover at least partially around a base of an electric discharge lamp,
- positioning a second section of the cover at least partially around a socket of a fixture,
- positioning an electrical contact of the base in electrical contact with an electrical contact of the socket, whereby the cover shields both the electrical contact of the base and the electrical contact of the socket from at least one of dripping liquid, light splashing liquid, and condensation wherein the cover at least partially interlocks with the base and the cover at least partially interlocks with the socket.

15. A process for providing environmental resistance to a germicidal system comprising:

positioning a first section of a cover at least partially around a base of an electric discharge lamp, positioning a second section of the cover at least partially around a socket of a fixture, positioning an electrical contact of the base in electrical contact with an electrical contact of the socket, whereby the cover shields both the electrical contact of the base and the electrical contact of the socket from at least one of dripping liquid, light splashing liquid, and condensation wherein the cover at least partially seals to the base and the cover at least partially seals to the socket.

16. A process for providing environmental resistance to a germicidal system comprising:

positioning a first section of a cover at least partially around a base of an electric discharge lamp, positioning a second section of the cover at least partially around a socket of a fixture, positioning an electrical contact of the base in electrical contact with an electrical contact of the socket, whereby the cover shields both the electrical contact of the base and the electrical contact of the socket from at least one of dripping liquid, light splashing liquid, and condensation positioning the base to engage a lamp holder, attached to the fixture, for mechanical support, wherein the cover at least partially abuts the base, the cover at least partially abuts the socket.

17. A process for providing environmental resistance to a germicidal system comprising:

positioning a first section of a cover at least partially around a base of an electric discharge lamp, positioning a second section of the cover at least partially around a socket of a fixture, positioning an electrical contact of the base in electrical contact with an electrical contact of the socket, whereby the cover shields both the electrical contact of the base and the electrical contact of the socket from at least one of dripping liquid, light splashing liquid, and condensation positioning the base to engage a lamp holder, attached to the fixture, for mechanical support, wherein the cover at least partially abuts the base, the cover at least partially abuts the socket, the electric discharge lamp is an germicidal lamp.

* * * * *